(12) United States Patent
Siess

(10) Patent No.: US 10,881,769 B2
(45) Date of Patent: Jan. 5, 2021

(54) PURGE-FREE MINIATURE ROTARY PUMP

(71) Applicant: Abiomed, Inc., Danvers, MA (US)

(72) Inventor: Thorsten Siess, Wuerselen (DE)

(73) Assignee: ABIOMED, INC., Danvers, MA (US)

(*) Notice: Subject to any disclaimer, the term of this patent is extended or adjusted under 35 U.S.C. 154(b) by 0 days.

(21) Appl. No.: 15/338,706

(22) Filed: Oct. 31, 2016

(65) Prior Publication Data

US 2017/0043074 A1 Feb. 16, 2017

Related U.S. Application Data

(63) Continuation of application No. 14/926,099, filed on Oct. 29, 2015, now Pat. No. 9,486,566, which is a continuation of application No. 11/934,001, filed on Nov. 1, 2007, now Pat. No. 9,199,020.

(51) Int. Cl.
| | | |
|---|---|---|
| *A61M 1/10* | (2006.01) | |
| *A61M 1/12* | (2006.01) | |
| *F04D 13/06* | (2006.01) | |
| *F04D 29/048* | (2006.01) | |

(Continued)

(52) U.S. Cl.
CPC .............. *A61M 1/101* (2013.01); *A61M 1/12* (2013.01); *F04D 13/06* (2013.01); *F04D 29/048* (2013.01); *F04D 29/18* (2013.01); *F04D 29/406* (2013.01); *A61M 1/1015* (2014.02); *A61M 1/1017* (2014.02); *A61M 1/1022* (2014.02); *A61M 1/1031* (2014.02); *A61M 1/122* (2014.02); *A61M 1/125* (2014.02)

(58) Field of Classification Search
CPC .. A61M 1/101; A61M 1/1015; A61M 1/1031; A61M 1/12
See application file for complete search history.

(56) References Cited

U.S. PATENT DOCUMENTS

| 5,964,694 A | 10/1999 | Siess et al. |
|---|---|---|
| 6,201,329 B1 | 3/2001 | Chen |
| 6,293,901 B1 | 9/2001 | Prem |

(Continued)

FOREIGN PATENT DOCUMENTS

| JP | 2003-503639 | 1/2003 |
|---|---|---|
| JP | 2003-528697 | 9/2003 |

(Continued)

OTHER PUBLICATIONS

Official Action dated Dec. 4, 2013 for Canadian Patent Application No. 2,704,196 (2 pages).

(Continued)

*Primary Examiner* — Tammie K Marlen
(74) *Attorney, Agent, or Firm* — Botos Churchill IP Law LLP

(57) ABSTRACT

Methods and systems are provided for the circulation of blood using a purge-free miniature pump. In one embodiment, a pump is provided that may comprise a housing including a rotor and a stator within a drive unit. In this embodiment, the pump may establish a primary blood flow through the space between the drive unit and the housing and a secondary blood flow between the rotor and stator. In another embodiment, a pump establishes a primary blood flow outside the housing and a secondary blood flow between the rotor and stator. In yet another embodiment, a method is provided for introducing the pump into the body and circulating blood using the pump.

16 Claims, 2 Drawing Sheets

(51) Int. Cl.
*F04D 29/18* (2006.01)
*F04D 29/40* (2006.01)

(56) References Cited

U.S. PATENT DOCUMENTS

| | | |
|---|---|---|
| 6,942,611 B2 | 9/2005 | Siess |
| 6,981,942 B2 | 1/2006 | Khaw et al. |
| 2001/0031210 A1 | 10/2001 | Antaki et al. |
| 2003/0100816 A1 | 5/2003 | Siess |
| 2009/0118567 A1 | 5/2009 | Siess |
| 2011/0238172 A1 | 9/2011 | Akdis |
| 2016/0045653 A1 | 2/2016 | Siess |

FOREIGN PATENT DOCUMENTS

| | | |
|---|---|---|
| WO | WO-96/18358 | 6/1996 |
| WO | WO-01/02724 | 1/2001 |

OTHER PUBLICATIONS

Office Action for Chinese Patent Application No. 200880114288.8, dated Mar. 20, 2012 (English translation) (10 pages).
Office Action for Chinese Patent Application No. 200880114288.8 dated Mar. 5, 2013 (English translation) (8 pages).
Examination Report for European Patent Application No. 08 845 862.5, dated Nov. 17, 2011 (10 pages).
Notice of Rejection for Japanese Patent Application No. 2010-532170, dated Feb. 27, 2013 (English translation) (2 pages).
International Preliminary Report on Patentability for International Patent Application No. PCT/US2008/081308, dated May 4, 2010 (10 pages).
International Search Report and Written Opinion for International Patent Application No. PCT/US2008/081308, dated Mar. 20, 2009 (19 pages).

PURGE-FREE MINIATURE ROTARY PUMP

CROSS-REFERENCE TO RELATED APPLICATIONS

This application is a continuation of U.S. patent application Ser. No. 14/926,099, filed Oct. 29, 2015 (allowed), which is a continuation of U.S. patent application Ser. No. 11/934,001, filed on Nov. 1, 2007, now U.S. Pat. No. 9,199,020, the disclosures of which are hereby incorporated by reference in their entities.

BACKGROUND OF INVENTION

Embodiments of this invention relate generally to, but are not limited to, the provision and use of medical devices and, more particularly, to the provision and use of miniature, implantable blood pumps for assisting or supplementing cardiac function.

SUMMARY OF INVENTION

At least some aspects and embodiments of the invention are directed to systems and methods for assisting the functioning of the human heart. In particular, one embodiment is directed to a system and method for pumping blood that utilizes a miniature blood pump with a tubular housing including a drive unit carrying an impeller, where the drive unit is maintained free of clots or other blood deposits without the use of a purge fluid.

Existing miniature blood pumps, such as that of U.S. Pat. No. 6,942,611, employ a purge fluid to maintain the motor section free of obstructions that could impair performance or, in the long term, cause seizure of the pump. While the purge fluid arrangement is relatively effective, the additional structure it requires may increase the risk of pump failure when the device is used for longer durations, such as those in excess of thirty days.

One embodiment in accord with the present invention includes a blood pump that may comprise a tubular housing in which an electromotive drive unit is located. The drive unit may be arranged coaxially within the housing, creating a primary blood flow channel in the annular space between the drive unit and the interior surface of the housing. In this configuration, blood is driven in a generally helical motion by an impeller arranged on the upstream side of the drive unit, circulates along the flow channel, and exits the housing through a laterally branching outlet tube.

The housing and the outlet tube may have an L-shaped configuration, whereby the pump may be inserted into a port created in the cardiac wall, while the outlet tube may be connected to a target vessel. In this configuration, the blood pump may serve to support the heart temporarily without being totally inserted into the heart like larger, intracardiac blood pumps.

One aspect of the invention is directed to a miniature blood pump that is maintained free of clots or other blood deposits or accumulations without the use of a purge fluid. The blood pump may include an annular, secondary flow channel constructed between the rotor and the stator, through which blood flows to continually flush the areas between the relatively moving parts of the rotor and stator. The secondary blood flow may be in a direction generally opposite the primary blood flow.

Another aspect of the invention is directed to a miniature axial blood pump in which a rotor carrying an impeller does not require mechanical support in the axial direction. The blood pump may employ a magnetic bearing that supports the rotor and impeller in the axial direction. In some embodiments, the axial magnetic bearing may be at least partially active.

Another aspect of the invention provides a catheter-based pump that employs the purge fluid free secondary blood flow path arrangement described above. In this device, the primary blood flow is directed outside and around the housing immediately behind the impeller, and additional ports positioned behind the rotor allow for the intake of blood to form the secondary blood flow.

Another aspect of the invention may provide for a catheter-based pump that employs a magnetic bearing to control the axial position of a rotor carrying an impeller. The magnetic bearing may be active, or passive, or both.

Another aspect of the invention is directed to method for providing cardiac assistance by the use of a miniature blood pump that includes a housing, a drive unit positioned within the housing and having a rotor and a stator, an impeller positioned at one end of the drive unit and connected to the rotor, and a cannula extending from the end of the housing nearest the impeller. The pump may be operated to create a primary blood flow around the drive unit and a secondary blood flow in an annular space formed between the rotor and the stator. The secondary blood flow may be generally in a direction opposite the primary blood flow. Axial support may be provided by mechanical bearings and/or by active or passive magnetic bearings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
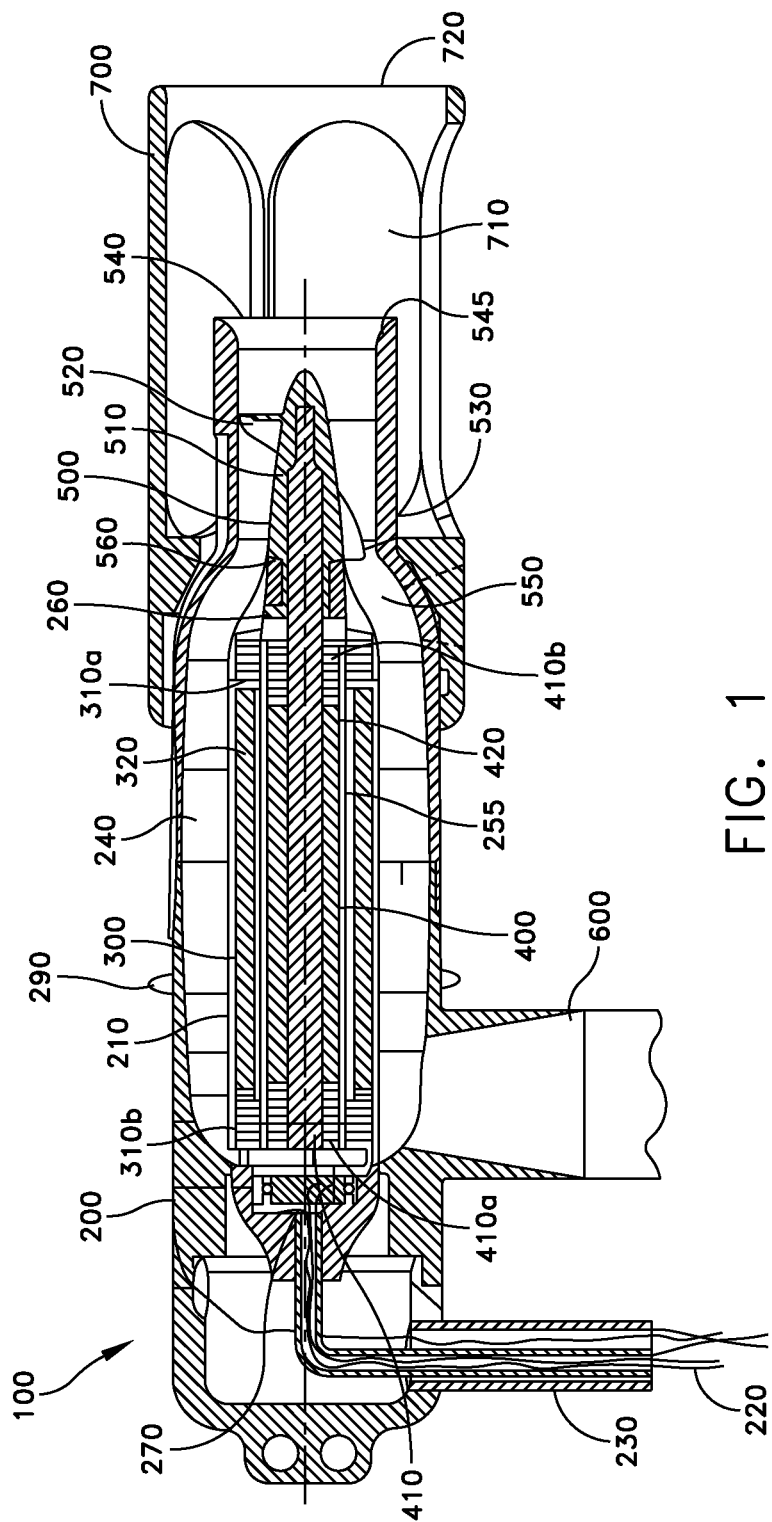
FIG. 1 is a schematic cross-section of one embodiment of a blood pump according to the present invention.

Various embodiments and aspects thereof will now be described in more detail with reference to the accompanying figures. It is to be appreciated that this invention is not limited in its application to the details of construction and the arrangement of components set forth in the following description or illustrated in the drawings. The invention is capable of other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments. Also, the phraseology and terminology used herein is for the purpose of description and should not be regarded as limiting. The use of "including," "comprising," "having," "containing," "involving," and variations thereof is meant to encompass the items listed thereafter and equivalents thereof as well as additional items.

A blood pump according to one embodiment of the invention is shown in schematic cross section in FIG. 1.

The blood pump 100 of this illustrative embodiment has an elongated, substantially cylindrical housing 200 in which a drive unit 210 is generally co-axially positioned. The drive unit 210 includes an electric motor comprising a stator portion 300 and a rotor portion 400. Electrical conductors 220 passing through a catheter 230 provide power and control signals to the electric motor.

The annular space between the drive unit 210 and the interior of the housing forms the primary blood flow path 240. In one embodiment, the inner and outer diameters of the primary blood flow path may be on the order of 7.0 and 10.0 mm, respectively, providing for a cross-sectional area in the primary blood flow path of approximately 160 mm$^2$.

The stator portion 300 comprises a pair of permanent stator bearing magnets 310a, 310b. One stator bearing magnet 310a is positioned near the upstream end of the stator, while the other stator bearing magnet 310b is fixed near the downstream end.

The stator bearing magnets 310a, 310b cooperate with permanent rotor bearing magnets 410a, 410b to form a pair of radial magnetic bearings. The radial bearings allow the rotor to rotate relative to the stator without significant radial contact and create an annular space to allow for a secondary blood flow path 255. The stator bearing magnets 310a, 310b and rotor bearing magnets 410a, 410b may be comprised of stacked thin disc magnets, tubular magnets with an axial magnetization, or any other appropriate magnetic arrangement.

In the illustrative embodiment, the inner and outer diameters of the secondary blood flow path 255 may be on the order of 3.2 and 3.8 mm, respectively, providing a cross-sectional area of approximately 3.3 mm$^2$.

Located on the stator portion 300 between the stator bearing magnets 310a, 310b is a stator motor magnet 320. The stator motor magnet 320 combines with a rotor motor magnet 420 to form an electromagnetic motor that may be driven by conventional means to cause rotation of the rotor 400.

In this embodiment, an impeller 500 is attached to the rotor 400. The impeller 500 includes a hub 510 and a plurality of vanes 520 that project from the hub 510. The vanes may take any appropriate shape and be of any appropriate number. The impeller 500 rotates in a cylindrical pump ring 530, the diameter of which is about the same as that of the envelope of the impeller 500. The upstream end of the pump ring 530 has an axial inlet 540 that includes an input bevel 545. The downstream end of the pump ring 530 is followed by an impeller-free transition region 550, within which the inside diameter continuously enlarges from that of the pump ring 530 to that of the inner diameter of the housing 200 surrounding the drive unit 210.

The operation of the rotor 400 creates a force that draws the rotor forward, i.e., in the direction opposite the blood flow. To prevent the rotor 400 from being drawn so far forward that it contacts the housing, an axial hydraulic bearing 260 may be positioned at the end of the rotor 400 that includes the impeller 500. The axial hydraulic bearing 260 serves to arrest the forward translation of the rotor 400. In this embodiment, the axial hydraulic bearing 260 is provided with a plurality of openings that allow blood to pass though the bearing. In some embodiments, the axial bearing may also be configured as a contact bearing, so as to physically arrest forward movement of the rotor 400, particularly where external forces are operating on the device or when the rotor is starting up or winding down.

In some embodiments, the axial position of the rotor 400 may be controlled by an axial magnetic bearing positioned at either end of the rotor, with or without the additional use of a mechanical contact bearing. In one embodiment, for example, the axial magnetic bearing may comprise a permanent axial housing magnet 270, positioned in the housing 200 near the end of the rotor 400 opposite the impeller 500, and cooperating with a permanent axial rotor magnet 410, positioned in the end of the rotor opposite the impeller 500. In another embodiment, the axial bearing may include an active magnetic bearing that operates alone or in conjunction with the passive magnetic bearing and/or mechanical contact bearing. In one embodiment, the axial magnetic bearing comprises a cylindrical passive magnet designed to counteract the axial forces encountered when the rotor 400 is up to speed, surrounded by an active magnet, designed to compensate for additional axial loads, such as those present during pre-load or after-load of the impeller. In some cases, the axial position of the impeller may be determined by measuring the back emf within the system, thus eliminating the need for an additional position sensor. In other cases, a separate position sensor may be employed to provide feedback concerning the position of the rotor and facilitate control by an active magnetic bearing.

Towards the downstream end of the flow channel 240, an outlet tube 600 laterally branches from the pump housing 200. This outlet tube 600 extends in a direction generally perpendicular to the flow channel 240. In some embodiments, the inner diameter of the outlet tube 600 may enlarge in the direction of flow. The enlargement may be on the order or 5-10 degrees or, in one particular embodiment, approximately 8 degrees.

In certain embodiments, there may be a pressure detection opening in the inner wall of the housing that communicates with the primary flow channel 240. From the pressure detection opening, a pressure channel may be in fluid communication with the lumen of a hose extending through the catheter 230. A pressure sensor may be connected at the proximal end of the catheter to detect the pressure at the place of the pressure detection opening within the primary flow channel 240. As an alternative, a local pressure sensor can be installed within the blood pump 100.

In some embodiments, a tubular cannula 700 may be mounted on the pump ring 530 and extend from the housing 200. The cannula 700 may have longitudinally extending slots 710 arranged about its periphery, and/or an axial opening 720 at the front end. The length of the cannula 700 may, in some cases, not exceed the length of the housing 200, including the pump ring 530.

In the illustrative embodiment, the outer diameter of the housing 200 is approximately 11 mm. The inner diameter of the housing in the region of the flow channel 240 is approximately 10 mm. The drive unit 210 has an outside diameter of approximately 7.0 mm. The inner diameter of the pump ring 530 is approximately 6 mm, the outer diameter of the cannula 700 is approximately 10 mm, and the inner diameter of the cannula 700 is approximately to 8 mm.

In this embodiment, the entire housing 200, including the pump ring 530, has a length of about 50 mm, and the portion of the cannula 700 projecting beyond the pump ring 530 has a length of about 35 mm.

The foregoing approximate dimensions are for the illustrative embodiment only, and it is to be understood that the dimensions may vary, proportionally or otherwise, in other embodiments of the invention.

The dimensions of this particular embodiment are expected to result in blood flow rates of from 1.5 to 3.0 m/s in the region of the pump ring 530, from 1.0 to 1.5 m/s in the region of the flow channel 240, and of 0.5 m/s in the region of the outlet tube 600. The drive unit 210 is configured to run at a relatively high rotational speed of from 10,000 to 33,000 rpm. At those speeds, the impeller 500 would move in the range of 4 to 6 l (liters) of blood per minute under physiological pressure conditions.

It is anticipated that exemplary device of FIG. 1 would, with the above dimensions, result in a flow rate in the secondary blood flow path 255 greater than approximately 20 ml/min, with a shear rate of less than 150 N/m², a transition time of less than approximately 200 ms, and that it would maintain the inner surfaces of the motor at or below approximately 44° C.

In order to maintain sufficient flow through the secondary flow path to prevent the accumulation of clots or other deposits in a miniature pump of this approximate size and configuration, it has been determined that the pressure differential between the secondary flow path and the primary flow path should be no less than approximately 60 mmHg.

In the illustrative embodiment, the desired pressure differential is achieved by use of the laterally branching outlet tube 600, described above, which creates a secondary pressure rise. In addition, as shown in FIG. 1, the secondary flow path 255 can be connected to the primary flow channel by means of a small gap 560 positioned behind the impeller 500 and running in a direction approximately perpendicular to the direction of flow through the primary flow channel. This gap 560 can help create a "water pump" effect that reduces the pressure within the secondary flow path 255 and helps to draw blood through the secondary flow path 255 in a direction opposite the flow through the primary flow path 240.

The exemplar paracardiac blood pump of FIG. 1 may be inserted though a puncture in the cardiac wall and introduced into the heart in such a manner that the housing 200 sealingly closes the puncture hole, while the cannula 700 is in the interior of the heart and the outlet tube 600 outside the heart. The puncture hole in the cardiac wall may be made without removing cardiac wall tissue. This facilitates the closing of the hole in the cardiac wall after the future withdrawal of the pump. For a better axial fixing of the pump on the cardiac wall, a peripheral enlargement 290 may be provided on the housing 200.

With the blood pump arranged as described above, an essential portion of the length of the housing 200 and the cannula 700 is located in the interior of the heart, while a relatively short portion of the housing 200 projects from the heart, and the outlet tube 600 together with a hose connected to the outlet tube 600 lies close against the outside of the heart. Therefore, the blood pump does not occupy substantial room within the chest cavity.

The blood pump may be implanted into the open heart to provide heart support for the duration of an operation or another intervention or to provide longer term support following an operation. An advantage of a miniature pump is that no heavy-weight and voluminous pumps need to be borne on the thoracic region of the patient. In addition, the pump is so small and light that even the fragile right or left atrium is not substantially deformed by applying and introducing the pump. In all cases, the positioning of the pump may be effected in a space-saving manner, and disturbances and impairments of the access to the heart being kept as low as possible.

Figure 2:
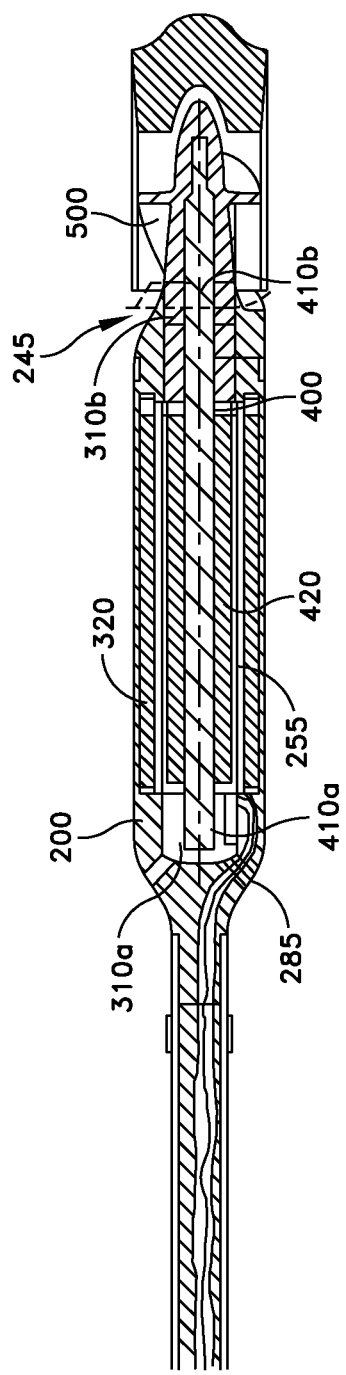
FIG. 2 is a schematic cross-section of one embodiment of a catheter-based blood pump according to the present invention.

The systems described above may also be employed in an intravascular, catheter-based device, as shown in FIG. 2. In this embodiment, a catheter-based pump includes a housing 200 that carries a stator motor magnet 320 and stator bearing magnets 310a, 310b. A rotor 400 carries a rotor motor magnet 420, rotor bearing magnets 410a, 410b, and an impeller 500. The rotor and stator bearing magnets cooperate to form forward and rear radial magnetic bearings.

In this embodiment, the rotating impeller creates a primary blood flow that passes outside the housing through primary blood flow openings 245. Secondary blood flow openings 285, located downstream of the primary blood flow openings 245 allow for a secondary blood flow path 255 between the rotor 400 and the housing 200 including the stator magnets. As in the embodiment of FIG. 1, this secondary blood flow path 255 is generally in a direction opposite the primary blood flow path. The flow of blood through the secondary blood flow path 255 serves to prevent the accumulation of clots or other blood deposits within the motor.

In this embodiment, an axial magnetic bearing, which may be passive, active, or both, may be located at the rear of the rotor and counteracts the forces drawing the rotor forward, as described above. In other embodiments, the axial forces may be addressed hydraulic or contact bearings.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A paracardial blood pump, comprising:
    a distal end configured as a blood flow inlet;
    a proximal end configured as a blood flow outlet;
    a tubular housing with a longitudinal axis,
    a drive unit arranged coaxially within the tubular housing, the drive unit comprising a rotor motor magnet and a stator motor magnet, the rotor motor magnet and the stator motor magnet configured to drive a rotation of an impeller positioned at one end of the drive unit;
    a longitudinally extending primary flow channel positioned between an interior wall of the housing and an exterior of the drive unit;
    a pump ring with an axial inlet positioned at one end of the tubular housing and surrounding at least a portion of the impeller, wherein the drive unit drives a rotation of the impeller within the pump ring;
    a cannula extending from an end of the tubular housing nearest the impeller;
    a laterally branching outlet tube positioned proximate an end of the tubular housing opposite the impeller, the laterally branching outlet tube positioned perpendicularly to the primary flow channel;
    a secondary flow channel formed between the rotor motor magnet and the stator motor magnet, the secondary flow channel configured to direct a flow of blood in a direction generally opposite a direction of blood flow through the primary flow channel wherein the primary flow channel and the secondary flow channel are in fluid communication with each other
    such that blood flows from the primary flow channel to the secondary flow channel in a direction perpendicular to the longitudinal axis and positioned proximally of the laterally branching outlet tube.

2. The paracardial blood pump of claim 1, further comprising a first radial magnetic bearing positioned in the drive unit near the impeller and a second radial magnetic bearing positioned towards an end of the drive unit opposite the impeller.

3. The paracardial blood pump of claim 2, wherein the secondary flow channel extends through the first radial magnetic bearing and the second radial magnetic bearing, the axial hydraulic bearing configured to arrest distal translation of the rotor motor magnet.

4. The paracardial blood pump of claim 1, further comprising an axial hydraulic bearing proximate the end of the drive unit nearest the impeller, the axial hydraulic bearing configured to arrest distal translation of the rotor motor magnet.

5. The paracardial blood pump of claim 4, wherein the axial hydraulic bearing comprises openings adapted to allow blood to flow from the secondary flow channel through the bearing and into the primary flow channel.

6. The paracardial blood pump of claim 1, further comprising an axial magnetic bearing proximate the end of the drive unit opposite the impeller.

7. The paracardial blood pump of claim 6, wherein the axial magnetic bearing is at least partially active.

8. A paracardial blood pump, comprising:
- a distal end configured as a blood flow inlet;
- a proximal end configured as a blood flow outlet;
- a drive unit arranged coaxially within a tubular housing, the drive unit comprising a rotor motor magnet and a stator motor magnet, the rotor motor magnet and the stator motor magnet configured to drive a rotation of an impeller positioned at one end of the drive unit;
- a longitudinally extending primary flow channel between an exterior of the drive unit and an interior wall of the tubular housing, and a secondary flow channel is formed between the rotor motor magnet and the stator motor magnet, the secondary flow channel configured to direct a flow of blood between the rotor and the stator in a direction generally opposite a direction of blood flow through the primary flow channel;
- a cannula extending from an end of the tubular housing nearest the impeller, the impeller configured to convey blood through the cannula to the primary flow channel;
- a laterally branching outlet tube positioned proximate an end of the tubular housing opposite the impeller, the laterally branching outlet tube positioned perpendicularly to the primary flow channel; and
- wherein the secondary flow channel and the primary flow channel are in fluid communication such that blood flows from the secondary flow channel to the primary flow channel the blood flowing perpendicularly to a longitudinal axis of the tubular housing and proximally of the laterally branching outlet tube.

9. The paracardial blood pump of claim 8, wherein the tubular housing comprises a blood inlet at a distal portion of the tubular housing, wherein the impeller is configured to convey blood into the tubular housing and through the tubular housing in a proximal direction.

10. The paracardial blood pump of claim 9, further comprising a pump ring with an axial inlet positioned at one end of the tubular housing and surrounding at least a portion of the impeller, wherein the primary flow channel extends through the axial inlet.

11. The paracardial blood pump of claim 10, wherein the pump ring comprises a blood outlet, wherein the impeller is configured to convey blood through the tubular housing and out of the paracardial blood pump through the blood outlet.

12. The paracardial blood pump of claim 8, further comprising a first radial magnetic bearing positioned in the drive unit near the impeller and a second radial magnetic bearing positioned towards an end of the drive unit opposite the impeller.

13. The paracardial blood pump of claim 8, further comprising an axial hydraulic bearing proximate the end of the drive unit nearest the impeller, the axial hydraulic bearing configured to arrest distal translation of the rotor.

14. The paracardial blood pump of claim 13, wherein the axial hydraulic bearing comprises openings adapted to allow blood to flow the secondary flow channel through the bearing and into the primary flow channel.

15. The paracardial blood pump of claim 8, further comprising an axial magnetic bearing proximate the end of the drive unit opposite the impeller.

16. The paracardial blood pump of claim 15, wherein the axial magnetic bearing is at least partially active.

* * * * *